US007763227B2

(12) United States Patent
Wang

(10) Patent No.: US 7,763,227 B2
(45) Date of Patent: Jul. 27, 2010

(54) PROCESS FOR THE MANUFACTURE OF CARBON DISULPHIDE

(75) Inventor: Dean Chien Wang, Missouri, TX (US)

(73) Assignee: Shell Oil Company, Houston, TX (US)

(*) Notice: Subject to any disclaimer, the term of this patent is extended or adjusted under 35 U.S.C. 154(b) by 0 days.

(21) Appl. No.: 12/441,172

(22) PCT Filed: Sep. 17, 2007

(86) PCT No.: PCT/EP2007/059746

§ 371 (c)(1),
(2), (4) Date: Mar. 13, 2009

(87) PCT Pub. No.: WO2008/034777

PCT Pub. Date: Mar. 27, 2008

(65) Prior Publication Data

US 2010/0028243 A1 Feb. 4, 2010

(30) Foreign Application Priority Data

Sep. 18, 2006 (EP) ................................. 06120802

(51) Int. Cl.
*C01B 17/20* (2006.01)

(52) U.S. Cl. ................. 423/443; 423/648.1; 423/658.2; 252/373; 518/700; 518/702

(58) Field of Classification Search ................. 423/443, 423/648.1, 658.2; 252/373; 518/700, 702
See application file for complete search history.

(56) References Cited

U.S. PATENT DOCUMENTS

| | | | | |
|---|---|---|---|---|
| 2,492,719 | A | 6/1943 | Thacker | 23/206 |
| 2,767,059 | A | 10/1956 | Adcock et al. | 23/206 |
| 3,087,788 | A | 4/1963 | Porter | 23/181 |
| 3,847,221 | A | 11/1974 | Allen et al. | 166/274 |
| 3,856,925 | A | 12/1974 | Kodera et al. | 423/416 |
| 4,122,156 | A | 10/1978 | Kittrell et al. | 423/443 |
| 4,476,113 | A | 10/1984 | Young et al. | 424/161 |
| 4,999,178 | A | 3/1991 | Bowman | 423/571 |
| 5,076,358 | A | 12/1991 | Kissel | 166/275 |
| 5,609,845 | A | 3/1997 | Cimini et al. | 423/648.1 |
| 6,497,855 | B1 | 12/2002 | Wachs | 423/648.1 |
| 7,601,320 | B2 * | 10/2009 | Van Dorp et al. | 423/443 |
| 2004/0146450 | A1 | 7/2004 | Stauffer | 423/443 |

FOREIGN PATENT DOCUMENTS

GB 1173344 12/1969

* cited by examiner

*Primary Examiner*—Timothy C Vanoy
(74) *Attorney, Agent, or Firm*—William E. Hickman

(57) ABSTRACT

A process for the manufacture of carbon disulfide comprising the following steps: (a) reacting carbon monoxide with hydrogen sulfide to form carbonyl sulfide and hydrogen; (b) contacting the carbonyl sulfide formed in step (a) with a catalyst effective for disproportionating carbonyl sulfide into carbon disulfide and carbon dioxide.

9 Claims, 2 Drawing Sheets

PROCESS FOR THE MANUFACTURE OF CARBON DISULPHIDE

The present application claims priority of European Patent Application No. 06120802.1 filed 18 Sep. 2006.

FIELD OF THE INVENTION

The invention provides a process for the manufacture of carbon disulphide from carbon monoxide and hydrogen sulphide. The process further results in the manufacturing of hydrogen and carbon dioxide.

BACKGROUND OF THE INVENTION

Carbon disulphide is typically manufactured by reacting light saturated hydrocarbons with elemental sulphur that is in the vapour phase according to the reaction equation:

$$C_nH_{2(n+1)}+(3n+1)S \rightarrow nCS_2+(n+1)H_2S$$

In GB 1,173,344 for example is disclosed a process for reacting vapour phase sulphur and propane in the absence of a catalyst under a pressure not exceeding 10 atmospheres in a reaction zone which is maintained at a temperature of 550 to 850° C.

In U.S. Pat. No. 3,087,788 is disclosed a process for producing carbon disulphide from hydrocarbon gas and vaporous sulphur in a non-catalytic reaction stage combined with, preferably followed by, a catalytic reaction stage, wherein both stages are operated at a pressure between 2 and 20 atmospheres and a temperature between 400 and 750° C.

It is also known to manufacture carbon disulphide by catalytically reacting liquid sulphur with a hydrocarbon. In U.S. Pat. No. 2,492,719 for example is disclosed a process for preparing carbon disulphide, wherein a suspension of catalyst in molten sulphur is contacted with a hydrocarbon gas at a temperature of approximately 500 to 700° C., under sufficient pressure to maintain the sulphur in liquid phase.

A disadvantage of using hydrocarbons as a carbon source for the manufacture of carbon disulphide is that the hydrogen atoms in the hydrocarbon react with the elemental sulphur to form hydrogen sulphide. As disposal of hydrogen sulphide to the atmosphere is highly undesired and almost always not allowed, expensive treatment is required, usually by conversion into elemental sulphur. It would be advantageous to use a carbon source without hydrogen atoms for carbon disulphide manufacture.

Before 1960, solid carbonaceous material such as charcoal was used as carbon source for carbon disulphide manufacture. Solid carbonaceous material was contacted with vaporized elemental sulphur at very high temperatures. These processes using solid carbonaceous material were, however, replaced by the above-mentioned processes using light hydrocarbons such as methane and propane as carbon source for environmental and safety reasons.

It is known to use carbon monoxide as carbon source for carbon disulphide manufacture. In US 2004/0146450, for example, is disclosed a two-reactor process for the manufacture of carbon disulphide from carbon monoxide and sulphur dioxide. Two catalytic reactions are operated in tandem. In a first reactor, carbon monoxide and sulphur dioxide are reacted in the presence of a catalyst to form carbonyl sulphide and carbon dioxide. In a second reactor, the carbonyl sulphide formed in the first reactor is catalytically converted into carbon disulphide and carbon dioxide. Carbon disulphide is continuously removed from the second reactor by a solvent.

Also in U.S. Pat. No. 4,122,156, a two-reactor process for the manufacture of carbon disulphide from carbon monoxide and sulphur dioxide is disclosed.

In U.S. Pat. No. 2,767,059 a one-step process is described to convert $H_2S$ and CO into $CS_2$. The only product in this process is $CS_2$.

In U.S. Pat. No. 4,999,178 a process scheme is described for the conversion of $H_2S$ into hydrogen and sulphur. The process does not produce any carbon disulfide. In the first step $H_2S$ is reacted with a recycle gas comprising $H_2S$, COS and $CS_2$ and with a pure $CO_2$ stream. No reaction between $H_2S$ and CO is described. The hydrogen produced in the reaction is produced via the shift-reaction ($CO+H_2O \rightarrow CO_2+H_2$).

SUMMARY OF THE INVENTION

It has now been found that carbon disulphide can be manufactured from carbon monoxide by reacting carbon monoxide with hydrogen sulphide to form carbonyl sulphide and hydrogen and then disproportionating the carbonyl sulphide formed into carbon disulphide and carbon dioxide.

Accordingly, the invention provides a process for the manufacture of carbon disulphide comprising the following steps:

(a) reacting carbon monoxide with hydrogen sulphide to form carbonyl sulphide and hydrogen;

(b) contacting the carbonyl sulphide formed in step (a) with a catalyst effective for disproportionating carbonyl sulphide into carbon disulphide and carbon dioxide.

An advantage of the process according to the invention as compared to the conventional carbon disulphide manufacturing process using hydrocarbons as carbon source is that no hydrogen sulphide is formed that would have to be recycled to a Claus unit for conversion into sulphur.

An advantage of the process according to the invention as compared to the known carbon disulphide manufacture processes that use carbon monoxide as carbon source, i.e. the processes as disclosed in US 2004/0146450 and U.S. Pat. No. 4,122,156 wherein carbon monoxide is reacted with sulphur dioxide, is that less carbon dioxide is co-produced. In the process according to the invention, one mole of carbon dioxide is co-produced with one mole of carbon disulphide, whereas in the processes of US 2004/0146450 and U.S. Pat. No. 4,122,156 five moles of carbon dioxide are co-produced with one mole of carbon disulphide. In the present process hydrogen is co-produced which may result in significant design and cost benefit when used and integrated in other processes.

The process according to the invention has particular advantages when operated in combination with the conversion of a hydrocarbonaceous feedstock into synthesis gas, i.e. a gaseous mixture mainly comprising carbon monoxide and hydrogen. Synthesis gas is typically produced for subsequent synthesis of hydrocarbons by the Fischer-Tropsch process, other chemical synthesis processes, e.g. methanol or ammonia synthesis, power generation in gas turbines or for hydrogen production. Often, the carbon monoxide to hydrogen ratio in synthesis gas is too large for the envisaged application and part of the carbon monoxide in the synthesis gas is therefore typically converted into hydrogen by subjecting the synthesis gas to water-gas shift conversion. Another way to solve this problem is to produce extra hydrogen, e.g. via reforming, especially steam methane reforming. Combining the process according to the invention with synthesis gas production has the advantage that part of the carbon monoxide is used for carbon disulphide manufacture, thereby decreasing the carbon monoxide to hydrogen ratio in the remaining synthesis gas to a more desirable level. Moreover, additional hydrogen is co-produced in the reaction of carbon monoxide with hydrogen sulphide. This additional hydrogen can advantageously be used to further decrease the carbon monoxide to hydrogen ratio of the remaining synthesis gas. The hydrogen made by the process of the invention may also be used in the upgrading of heavy oil fractions, e.g. hydrocracking, hydrogenation etc., or for the generation of electricity.

Another advantage is that hydrogen sulphide is typically available at synthesis gas production locations, since the hydrocarbonaceous feedstock typically comprises sulphur compounds. If the sulphur compound is hydrogen sulphide, such as is the case for sour natural gas, the hydrogen sulphide will typically be separated from the hydrocarbonaceous feedstock before gasification. If the feedstock comprises other sulphur compounds, the feedstock may be hydrodesulphurized before gasification, thus producing hydrogen sulphide. A further advantage is that the hydrogen atoms of the hydrocarbonaceous compound are converted into valuable hydrogen. The carbon monoxide that is co-produced serves as a hydrogen-free feedstock for carbon disulphide manufacture and, thus, hydrogen sulphide formation is avoided.

DETAILED DESCRIPTION OF THE INVENTION

Figure 1:
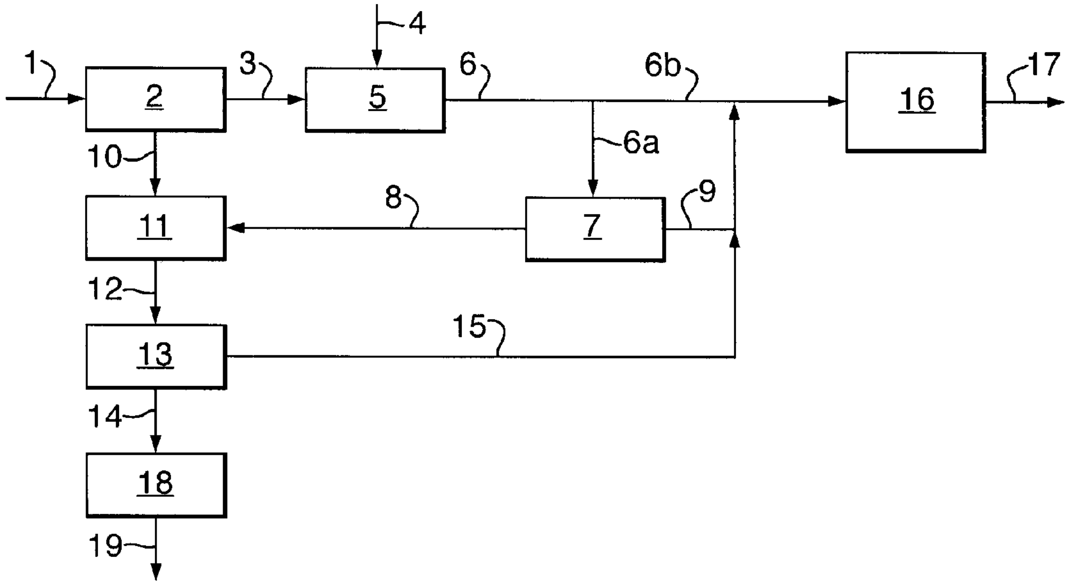
In FIG. 1 is shown a process scheme for manufacturing carbon disulphide and liquid hydrocarbons from sour natural gas.

In the process according to the invention, carbon monoxide is first reacted with hydrogen sulphide to form carbonyl sulphide and hydrogen according to:

$$CO+H_2S \rightarrow COS+H_2 \quad (1)$$

This reaction is known in the art, for example from U.S. Pat. Nos. 5,609,845 and 6,497,855 B1. The reaction may be carried out in any suitable way known in the art. Typically, the reaction will be carried out by contacting gaseous carbon monoxide and gaseous hydrogen sulphide with a catalyst. Suitable catalysts are for example those described in U.S. Pat. No. 5,609,845, the disclosure of which is incorporated herein by reference, for example mixed metal sulphides, sulphides of transition metals, in particular silica-supported metal sulphides. Typical reaction temperatures for step (a) are in the range of from 120 to 750° C.

The carbonyl sulphide formed in step (a) of the process according to the invention is then contacted in step (b) with a catalyst effective for disproportionating carbonyl sulphide into carbon disulphide and carbon dioxide according to:

$$2COS \Leftrightarrow CS_2+CO_2 \quad (2)$$

Preferably, the hydrogen formed in step (a) is separated from the carbonyl sulphide formed in step (a) before the carbonyl sulphide is disproportionated. This separation may be done by any suitable conventional technique, for example by selective absorption, adsorption, rectification or molecular sieving. Pressure Swing Absorption (PSA) and membrane separation are particular suitable separation processes. Another suitable method is cryogenic separation, e.g. low temperature distillation.

Catalysts effective for disproportionation of carbonyl sulphide are known in the art, for example from US 2004/0146450 and U.S. Pat. No. 4,122,156. Preferably, the catalyst comprises one or more metal oxides. Examples of suitable catalysts are alumina, titania, alumina-titania, silica-alumina, quartz, or clay, for example kaolin. The catalyst preferably has a specific surface area of at least 50 $m^2/g$, more preferably at least 100 $m^2/g$, even more preferably at least 200 $m^2/g$. Particularly preferred catalysts are gamma-alumina, titania, alumina-titania, or silica-alumina.

The reaction conditions under which the carbonyl sulphide is contacted with the disproportionation catalyst may be any reaction conditions known to be suitable for that reaction, for example the conditions as disclosed in US 2004/0146450 and U.S. Pat. No. 4,122,156.

Disproportionation reaction (2) is a thermodynamically unfavourable, reversible reaction. Since the heat of reaction is close to zero, the equilibrium constant does not change much with temperature. If desired, the carbonyl sulphide conversion can be increased by removing carbon disulphide from the reaction mixture, for example by solvent extraction or condensation.

The carbon monoxide that is reacted with hydrogen sulphide in step (a) may be carbon monoxide from any suitable source. Preferably the carbon monoxide is from a synthesis gas stream. Therefore, the process according to the invention preferably further comprises the following step:

(c) partially oxidizing a hydrocarbonaceous feedstock to obtain synthesis gas comprising carbon monoxide and hydrogen;

wherein the carbon monoxide that is reacted in step (a) is carbon monoxide obtained in step (c).

Partial oxidation of hydrocarbonaceous feedstocks to produce synthesis gas is known in the art. The hydrocarbonaceous feedstock may be any suitable feedstock, for example a stream containing gaseous, liquid or solid hydrocarbons, such as natural gas, distillate streams, residuum of atmospheric or vacuum distillation of crude oil, tar sand-derived bitumen, residuum of atmospheric or vacuum distillation of tar sand-derived bitumen, or coal. Also lignocellulosic biomass streams, for example wood, straw, corn stover, bagasse or the like, may be used as hydrocarbonaceous feedstock.

In the partial oxidation of hydrocarbonaceous feedstocks, synthesis gas is formed. Synthesis gas mainly comprises carbon monoxide and hydrogen, and, if air is used as oxidant for the partial oxidation reaction, also nitrogen. Synthesis gas may comprise minor amounts of other gaseous compounds, for example carbon dioxide, steam, hydrogen sulphide, and carbonyl sulphide.

The process according to the invention has particular advantages if the carbon monoxide that is reacted in step (a) is obtained by partial oxidation of a hydrocarbonaceous feedstock and the synthesis gas produced by the partial oxidation is used for hydrocarbon or methanol synthesis or another application that needs synthesis gas with a carbon monoxide to hydrogen ratio that is lower than the ratio obtained by the partial oxidation step. By using part of the carbon monoxide for the manufacture of carbon disulphide, the carbon monoxide to hydrogen ratio of the remainder of the synthesis gas is decreased to a more desirable level. By adding the hydrogen formed in step (a) of the process according to the invention to the remainder of the synthesis gas, the ratio can even be further decreased. Thus, there is no need to convert part of the carbon monoxide into hydrogen by water-gas shift conversion and/or to produce additional hydrogen by for example steam methane reforming.

Therefore, in a preferred embodiment of the invention, part of the carbon monoxide obtained in step (c) is reacted with hydrogen sulphide in step (a) and the remainder of the carbon monoxide and the hydrogen obtained in step (c) are used for hydrocarbon synthesis in a Fischer-Tropsch process or for methanol synthesis. More preferably, the hydrogen formed in step (a) is, together with the remainder of the carbon monoxide and the hydrogen obtained in step (c), used for hydrocarbon synthesis in a Fischer-Tropsch process or for methanol synthesis. The above is particularly relevant for processes starting with feedstocks having a low H/C ratio, e.g. coal.

Reacting part of the carbon monoxide obtained in step (c) with hydrogen sulphide may be done by contacting part of the synthesis gas stream obtained in step (c) with hydrogen sulphide in a reactor for step (a). Preferably, part of the carbon monoxide in the synthesis gas stream obtained in step (c) is first separated from the synthesis gas stream before being reacted with hydrogen sulphide in step (a). This may be done by separating at least part of the synthesis gas stream into a stream enriched in hydrogen and a stream enriched in carbon monoxide. The separation may be carried out by any suitable means known in the art, for example pressure swing absorption or membrane separation. The stream enriched in hydrogen may be substantially pure hydrogen, for example in case a hydrogen-selective membrane is used for the separation. The stream enriched in carbon monoxide is then contacted with the hydrogen sulphide in step (a) of the process according to the invention. The carbon monoxide concentration in that stream may vary, depending on the composition of the synthesis gas and the separation method used. Preferably, the carbon monoxide concentration in the stream enriched in carbon monoxide is in the range of from 70 to 100 vol %.

In another preferred embodiment of the invention, substantially all carbon monoxide that is obtained in step (c) is reacted with hydrogen sulphide in step (a). Reference herein to substantially all carbon monoxide is to at least 95 vol % of the carbon monoxide, preferably at least 99 vol %. The hydrogen obtained in step (c) can then advantageously be used for applications that need a relatively pure stream of hydrogen, for example generation of electricity in a hydrogen turbine or in a fuel cell, or ammonia manufacture. More preferably, the hydrogen formed in step (a) is, together with the hydrogen obtained in step (c), used for such applications.

Thus, in a preferred embodiment of the invention, substantially all carbon monoxide obtained in step (c) is reacted with hydrogen sulphide in step (a) and the hydrogen obtained in step (c) is used for generation of electricity in a hydrogen turbine or a fuel cell. More preferably, the hydrogen formed in step (a) is, together with the hydrogen obtained in step (c), used for generation of electricity in a hydrogen turbine or in a fuel cell.

Reacting substantially all carbon monoxide obtained in step (c) with hydrogen sulphide in step (a) can be done either by contacting the whole synthesis gas stream obtained in step (c) with hydrogen sulphide in a reactor for step (a), or by first separating the synthesis gas stream into a stream enriched in carbon monoxide that comprises substantially all carbon monoxide formed in step (c) and a stream enriched in hydrogen. The stream enriched in carbon monoxide is then contacted with hydrogen sulphide in a reactor for step (a). In this case, the stream enriched in hydrogen contains substantially no carbon monoxide and can suitably be used, optionally after further purification steps, for generation of electricity in a hydrogen turbine or a fuel cell, manufacture of ammonia, or in hydroconversion processes for crude oil refining such as hydrocracking, hydrodesulphurization, hydrogenation, or other known applications for relatively pure hydrogen.

If the whole synthesis gas stream obtained in step (c) is reacted with hydrogen sulphide, the hydrogen obtained in step (c) will be present in the reaction effluent of step (a) together with the hydrogen formed in step (a). Preferably, the hydrogen in the effluent is then separated from the carbonyl sulphide and unconverted reactants and used for an application that needs a relatively pure stream of hydrogen, optionally after further purification steps.

The hydrogen sulphide that is reacted with carbon monoxide in step (a) may be hydrogen sulphide from any source. In case the carbon monoxide is obtained via partial oxidation step (c), the hydrogen sulphide is preferably hydrogen sulphide that is either separated from the hydrocarbonaceous feedstock or obtained from sulphur compounds in the hydrocarbonaceous feedstock. Hydrogen sulphide may for example be obtained from such sulphur compounds by hydrodesulphurization of the feedstock or in partial oxidation step (c). Also hydrogen sulphide extracted from sour natural gas may be used.

In a preferred embodiment of the invention, the hydrocarbonaceous feedstock is natural gas that comprises hydrogen sulphide, i.e. sour natural gas, and at least part of the hydrogen sulphide that is reacted with carbon monoxide in step (a) is hydrogen sulphide that is separated from the natural gas. Separation of hydrogen sulphide from a hydrocarbonaceous feedstock that comprises hydrogen sulphide may done by any suitable technique known in the art, for example by physical absorption in an organic solvent followed by solvent regeneration.

In step (b) of the process according to the invention, carbon disulphide and carbon dioxide are formed. The carbon disulphide may be separated from the carbon dioxide and the unreacted carbonyl sulphide, for example by condensation or solvent extraction. Alternatively, a mixture comprising carbon disulphide, carbon dioxide and unreacted carbonyl sulphide may be obtained. Carbon disulphide that is separated from the carbon dioxide and the unreacted carbonyl sulphide may be used for conventional applications of carbon disulphide, for example as raw material for rayon production or as solvent.

It is known that carbon disulphide may be used as solvent for enhanced oil recovery by miscible flooding. In enhanced oil recovery by miscible flooding, a solvent for oil is introduced into an oil reservoir and driven through the reservoir to increase oil recovery from the reservoir beyond what can be achieved by conventional means. In U.S. Pat. No. 3,847,221 for example, the use of carbon disulphide for enhanced oil recovery from tar sands is disclosed.

Preferably, the process according to the invention further comprises injecting at least part of the carbon disulphide formed in step (b) in an oil reservoir for enhanced oil recovery. The carbon disulphide injected may be relatively pure carbon disulphide that is separated from the carbon dioxide formed and from the unreacted carbonyl sulphide. For enhanced oil recovery, it is however not necessary to use pure carbon disulphide. The enhanced oil recovery solvent may for example comprise a substantial amount of carbon dioxide. Therefore, the carbon disulphide injected is preferably in the form of a mixture with carbon dioxide formed in step (b) and unreacted carbonyl sulphide. Also other liquid components or streams may be mixed with the carbon disulphide before the carbon disulphide is injected into the oil reservoir.

The process according to the invention is particularly suitable for enhanced recovery of the hydrocarbonaceous feedstock that is used in partial oxidation step (c). Especially in the case of solid or semi-solid hydrocarbonaceous feedstocks, such as coal or tar-sand bitumen, the carbon disulphide that is manufactured may be advantageously used to recover the hydrocarbonaceous feedstock.

Instead of directly injecting the carbon disulphide formed in step (b) into an oil reservoir, all or part of the carbon disulphide formed in step (b) may be first be converted into a salt of a tri or tetrathiocarbonic acid. Such salt may be then be introduced into an oil reservoir for enhanced oil recovery under conditions leading to decomposition of the salt into free carbon disulphide. Enhanced oil recovery by using salts of tri or tetrathiocarbonic acid is known in the art, for example from U.S. Pat. No. 5,076,358. In a preferred embodiment of the invention, part of the carbon disulphide formed in step (b) is reacted with hydrogen sulphide and ammonia that is formed with hydrogen obtained in partial oxidation step (c) and/or carbon monoxide conversion step (a) to form ammonium thiocarbonate. Ammonium thiocarbonate can for example be prepared as disclosed in U.S. Pat. No. 4,476,113.

DETAILED DESCRIPTION OF THE DRAWINGS

Figure 2:
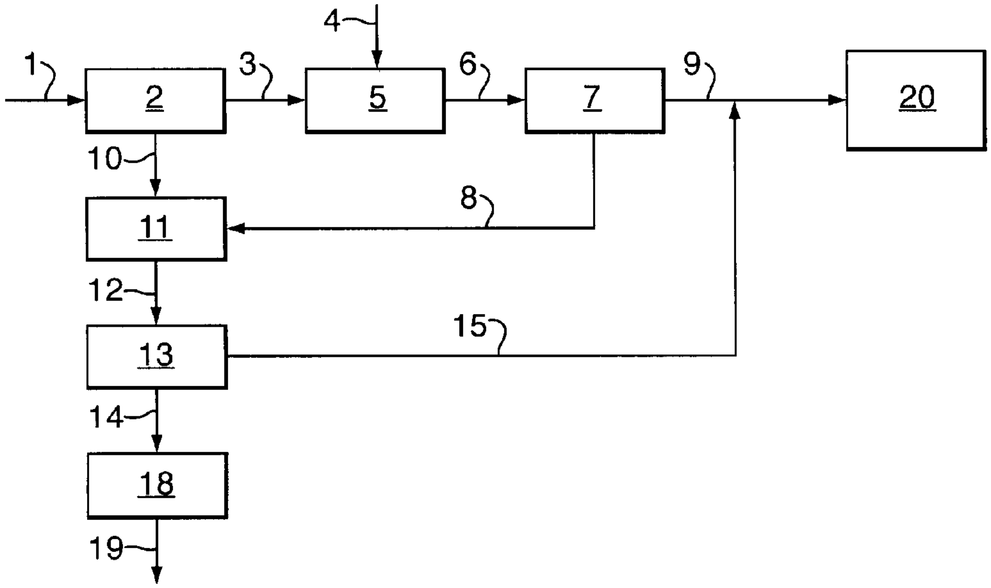
In FIG. 2 is shown a process scheme for manufacturing carbon disulphide and hydrogen for electricity generation from sour natural gas.
Figure 3:
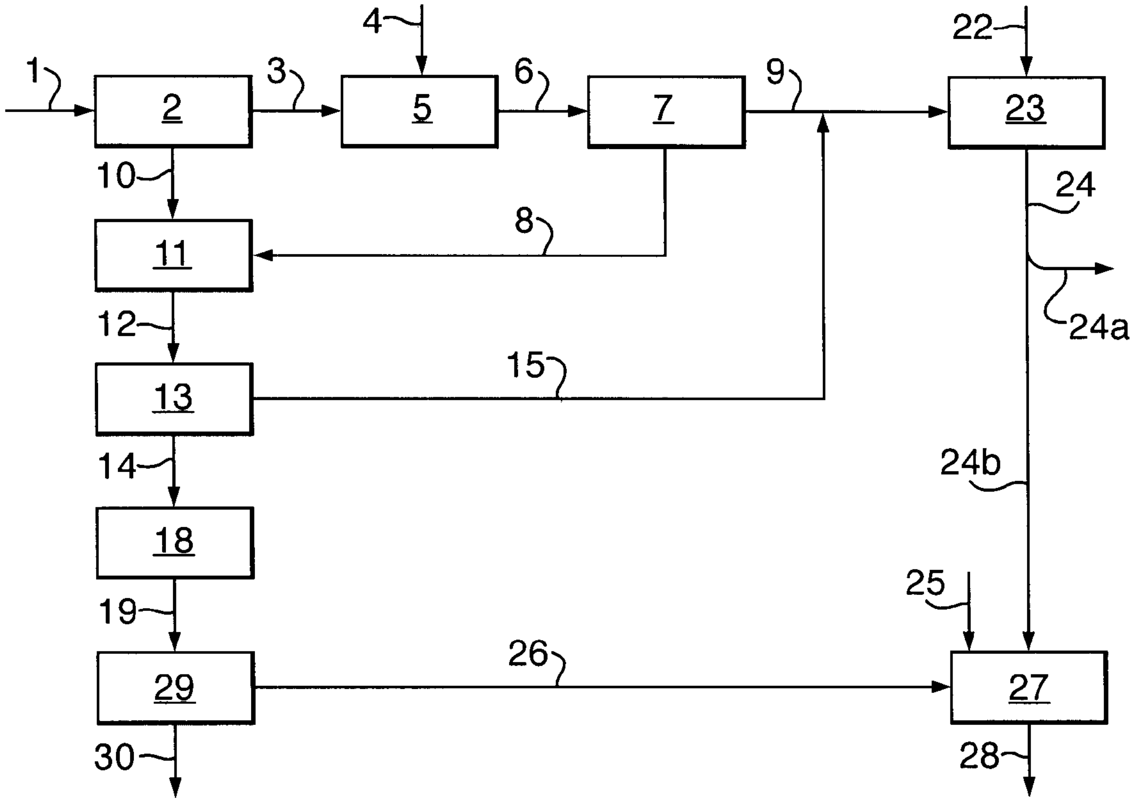
In FIG. 3 is shown a process scheme for manufacturing carbon disulphide, ammonia and ammonium thiocarbonate from sour natural gas.

Referring now to FIGS. 1 to 3, each schematically showing a process scheme of an embodiment of the invention, the invention is further illustrated. For parts of the process that are the same, the same reference numbers are used as in all three Figures.

In FIG. 1 is shown a process scheme for manufacturing both carbon disulphide and liquid hydrocarbons from sour natural gas. A stream of natural gas 1 that comprises hydrogen sulphide, i.e. sour natural gas, is supplied to a hydrogen sulphide removal unit 2. Desulphurized natural gas 3 and a molecular oxygen containing gas 4 are supplied to partial oxidation unit 5. In partial oxidation unit 5, the natural gas feedstock 3 is partially oxidised and a synthesis gas stream 6 mainly comprising carbon monoxide and hydrogen is obtained. Part 6*a* of synthesis gas stream 6 is supplied separator 7 and separated into a gas stream enriched in carbon monoxide 8 and a gas stream enriched in hydrogen 9.

The gas stream enriched in carbon monoxide 8 is, together with hydrogen sulphide 10 that is separated from the sour natural gas 1 supplied to reactor 11 for the conversion of carbon monoxide and hydrogen sulphide into carbonyl sulphide and hydrogen. A mixture 12 comprising carbonyl sulphide and hydrogen formed in reactor 11 is supplied to separation step 13 and separated into a stream comprising carbonyl sulphide 14 and hydrogen 15. The hydrogen 15 is added to gas stream enriched in hydrogen 9 from separator 7 and combined with the part 6*b* of synthesis gas stream 6 that was not sent to separator 7. The combined streams 6*b*, 9, and 15 are supplied to a reactor for hydrocarbon synthesis 16 for the manufacture of hydrocarbons by the Fischer-Tropsch process. Alternatively, the combined streams 6*b*, 9, and 15 may be supplied to a reactor for methanol synthesis (not shown). In another alternative embodiment of the invention (not shown), streams 6*b* and 9 are combined and supplied to a reactor for hydrocarbon synthesis and stream 15 is supplied to a fuel cell or a hydrogen turbine for electricity generation.

The stream comprising carbonyl sulphide 14 is supplied to disproportionation reactor 18. In reactor 18, a reaction mixture comprising carbon disulphide, carbon dioxide and unconverted carbonyl sulphide is formed. The reaction mixture 19 is withdrawn from reactor 18. Carbon disulphide may be separated from mixture 19 by conventional separation means (not shown) and then for example used for enhanced oil recovery. Alternatively, mixture 19 is used as such as solvent for enhanced oil recovery.

In FIG. 2 is shown a process scheme for manufacturing both carbon disulphide and hydrogen for electricity generation from sour natural gas. In the embodiment of the invention as shown in FIG. 2, the whole synthesis gas stream 6 is separated into separator 7 into a gas stream enriched in carbon monoxide 8 and a gas stream enriched in hydrogen 9. The hydrogen 15, i.e. the hydrogen formed in step (a) of the process in reactor 11 and subsequently separated from the carbonyl sulphide, is combined with gas stream enriched in hydrogen 9 and the combined stream is supplied to fuel cell 20 for electricity generation. Alternatively, the combined stream may be supplied to a hydrogen turbine (not shown) for electricity generation.

In FIG. 3 is shown a process scheme for manufacturing carbon disulphide, ammonia and ammonium thiocarbonate from sour natural gas.

In the embodiment of the invention as shown in FIG. 3, the whole synthesis gas stream 6 is separated into separator 7 into a gas stream enriched in carbon monoxide 8 and a gas stream enriched in hydrogen 9. The hydrogen 15, i.e. the hydrogen formed in step (a) of the process in reactor 11 and subsequently separated from the carbonyl sulphide, is combined with gas stream enriched in hydrogen 9. The combined hydrogen streams and stream of nitrogen 22 are supplied to ammonium reactor 23 to form ammonia 24. Part 24*a* of the ammonia is recovered from the process, for example for use in fertilizers. Part 24*b* of the ammonia is reacted with hydrogen sulphide 25 and carbon disulphide 26 in reactor 27 to form ammonium thiocarbonate 28. Carbon disulphide 26 is separated from reaction mixture 19 in separator 29. The remainder 30 of reaction mixture 19 may, if it still comprises carbon disulphide, be used as solvent for enhanced oil recovery. Alternatively, part of the separated carbon disulphide 26 is directly injected into an oil reservoir for enhanced oil recover and part is supplied to reactor 27 for conversion into ammonium thiocarbonate.

Further process integration may be obtained by using hydrogen sulphide separated from the sour natural gas 1 in hydrogen sulphide removal unit 2 as hydrogen sulphide 25 for the ammonium thiocarbonate manufacture. The nitrogen stream 22 that is supplied to ammonium reactor 23 may be obtained by air separation (not shown). The oxygen thus obtained may then be supplied as molecular oxygen containing gas 4 to partial oxidation unit 5.

That which is claimed is:

1. A process for the manufacture of carbon disulphide comprising the following steps:

(1) providing a hydrocarbon feedstock comprising hydrogen sulfide;

(2) separating at least a portion of the hydrogen sulfide from the hydrocarbon feedstock:

(3) partially oxidizing at least a portion of the hydrocarbon feedstock from step 2 into a synthesis gas comprising carbon monoxide and hydrogen;

(4) separating at least a portion of the hydrogen from the synthesis gas from step 3, leaving a carbon monoxide enriched synthesis gas;

(5) reacting carbon monoxide from step 4 with hydrogen sulphide from step 2 to form carbonyl sulphide and hydrogen;

(6) contacting the carbonyl sulphide from step 5 with a catalyst effective for disproportionating carbonyl sulphide into carbon disulphide and carbon dioxide.

2. A process according to claim 1, wherein part of the carbon monoxide obtained in step 3 is reacted with hydrogen sulphide in step 5 and the remainder of the carbon monoxide and the hydrogen obtained in step 3 are used for hydrocarbon synthesis in a Fischer-Tropsch process or for methanol synthesis.

3. A process according to claim 2, wherein the hydrogen formed in step 5 is, together with the remainder of the carbon monoxide and the hydrogen obtained in step 3, used for hydrocarbon synthesis in a Fischer-Tropsch process or for methanol synthesis.

4. A process according to claim 1, wherein substantially all carbon monoxide obtained in step 3 is reacted with hydrogen sulphide in step 5 and the hydrogen obtained in step 3 is used for generation of electricity in a hydrogen turbine or a fuel cell.

5. A process according to claim 4, wherein the hydrogen formed in step 5 is, together with the hydrogen obtained in step 3, used for generation of electricity in a hydrogen turbine or in a fuel cell.

6. A process according to claim 1, wherein the hydrocarb feedstock is natural gas.

7. A process according to claim 1, further comprising injecting at least part of the carbon disulphide formed in step 6 in an oil reservoir for enhanced oil recovery.

8. A process according to claim 1, further comprising injecting at least part of the carbon disulphide and carbon dioxide as a mixture formed in step 6 in an oil reservoir for enhanced oil recovery.

9. A process according to claim 1, further comprising injecting at least part of the carbon disulphide and carbon dioxide formed in step 6, together with any unreacted carbonyl sulfide from step 6 as a mixture in an oil reservoir for enhanced oil recovery.

* * * * *